(12) United States Patent
Stevenson

(10) Patent No.: US 7,507,527 B2
(45) Date of Patent: Mar. 24, 2009

(54) DETECTION OF HUMAN IMMUNODEFICIENCY VIRUS

(75) Inventor: Mario Stevenson, Shrewsbury, MA (US)

(73) Assignee: University of Massachusetts, Boston, MA (US)

( * ) Notice: Subject to any disclaimer, the term of this patent is extended or adjusted under 35 U.S.C. 154(b) by 313 days.

(21) Appl. No.: 10/795,580

(22) Filed: Mar. 8, 2004

(65) Prior Publication Data

US 2005/0064393 A1    Mar. 24, 2005

Related U.S. Application Data

(63) Continuation of application No. 10/044,197, filed on Jan. 10, 2002, now abandoned, which is a continuation of application No. 09/478,170, filed on Jan. 5, 2000, now abandoned.

(60) Provisional application No. 60/115,228, filed on Jan. 8, 1999.

(51) Int. Cl.
    *C12Q 1/70* (2006.01)
(52) U.S. Cl. ............... 435/5; 435/6; 435/91.2; 536/23.1
(58) Field of Classification Search ........ None
    See application file for complete search history.

(56) References Cited

U.S. PATENT DOCUMENTS

| 5,703,086 | A | 12/1997 | Bukrinsky et al. ......... 514/275 |
| 5,753,674 | A | 5/1998 | Kun et al. ............... 514/309 |
| 5,872,210 | A | 2/1999 | Medabalimi ............. 530/327 |
| 6,331,389 | B1 | 12/2001 | Lieven et al. |
| 6,797,464 | B2 | 9/2004 | Stevenson et al. |
| 7,232,657 | B2 | 6/2007 | Stevenson et al. |

OTHER PUBLICATIONS

Zazzi et al. J. Medical Virology, 1997, vol. 52, p. 20-25.*
Bukrinsky et al. PNAS, 1992, vol. 89, p. 6580-6584.*
Chun et al. PNAS, 1997, vol. 94, p. 13193-13197.*
Tan et al. PNAS, 1998, vol. 95, p. 4247-4252.*
Bisset et al., "Highly active antiretroviral therapy during early HIV infection reverses T-cell activation and maturation abnormalities", AIDS 12:2115-23 (1998).
Brown et al. "Correct Integration of . . . ," Cell, vol. 49, pp. 347-356, 1987.
Bukrinsky et al., "Active nuclear import of . . . ," Proc. Natl. Acad. Sci. USA, vol. 89, pp. 6580-6584, 1992.
Chun et al., "Presence of an inducible HIV-1 latent resevoir during highly active antiretroviral therapy", Proc. Natl. Acad. Sci. 94:13193-97 (1997).
Jurriaans et al., "Analysis of human immunodeficiency . . . ," Journal of General Virology, vol. 73, pp. 1537-1541, 1992.
Panther et al., "Unintegrated Circular HIV-1 . . . ," Journal of Acquired Immune Deficiency Syndromes and Human Retrovirology, vol. 17, pp. 303-313, 1998.
Pauza et al., "2-LTR Circular Viral DNA . . . ," Virology, vol. 205, pp. 470-478, 1994.
Stevenson et al., "HIV-1 replication is . . . ," The EMBO Journal, vol. 9, No. 5, pp. 1551-1560, 1990.
Stevenson et al., "Integration Is Not Necessary . . . ," Journal of Virology, pp. 2421-2425, 1990.
Zazzi et al., "Evaluation of the presence of 2-LTR HIV-1 unitegrated DNA as a simple molecular predictor of disease progression", J. Med. Virol. 52:20-25 (1997).
Bukrinsky et al., "Human immunodeficiency virus type 1 2-LTR circles reside in a nucleoprotein complex which is different from the preintegration complex," J. Virol. 67(11):6863-6865 (1993).
Munoz-Fernandez et al., "Quantification of low levels of human immunodeficiency virus (HIV) type 1 RNA in P24 antigen-negative, asymptomatic, HIV-positive patients by PCR," J. Clin. Microbiol. 34(2):404-408 (1996).
Sharkey et al., "Persistence of episomal HIV-1 infection intermediates in patients on highly active anti-retroviral therapy," Nat. Med. 6(1):76-81 (2000).
Tedder et al., "Comparison of culture- and non-culture-based methods for quantification of viral load and resistance to antiretroviral drugs in patients given zidovudine monotherapy," J. Clin. Microbiol. 36(4):1056-1063 (1998).
Albrecht et al., "Highly active antiretroviral therapy significantly improves the prognosis of patients with HIV-associated progressive multifocal leukoencephalopathy," AIDS, 12, pp. 1149-1154 (1998).
Andreoni et al., "Correlation between changes in plasma HIV RNA levels and in plasma infectivity in respone to antiretroviral therapy," AIDS Research and Human Retroviruses, 13:7, pp. 555-561 (1997).
Bruisten et al., "Cellular proviral HIV type 1 DNA load persists after long-term RT-inhibitor therapy in HIV type 1 infected persons," AIDS Research and Human Retroviruses, 14:12, pp. 1053-1058 (1998).
Bukrinsky et al., "Components of HIV-1 preintegration complex is associated with complex maturation," VIII Intl. Cong. AIDS/III STD World Cong. PoA 2252 (1992).

(Continued)

*Primary Examiner*—Bruce Campell
*Assistant Examiner*—Agnieszka Boesen
(74) *Attorney, Agent, or Firm*—Fish & Richardson P.C.

(57) ABSTRACT

The invention relates to a method of detecting a HIV-infected cell in a mammal. The method includes detecting an HIV 2-LTR circle DNA molecule obtained from a cell of an HIV-positive mammal, especially an HIV-1-positive human.

24 Claims, 2 Drawing Sheets

OTHER PUBLICATIONS

Bukrinsky et al., "Nuclear transport of HIV-1 genetic material: Implications for latency and pathogenesis," Keystone Symp. Prev. Treat. AIDS, J.Cell Biochem. Suppl. 0 (16 part E), 46 (1992) (abstract only).

Bukrinsky et al., "Quiescent T lymphocytes as an inducible virus reservoir in HIV-1 infection," Science, 254:5030, pp. 423-427 (1991).

Chun et al., "Latent reservoirs of HIV: Obstacles to the eradication of virus," Proc. Natl. Acad. Sci. USA, 96, pp. 10958-10961 (1999).

Clayman et al., "Circular forms of DNA synthesized by rous sarcoma virus in vitro," Science, 206, pp. 582-584 (1979).

D'Aquila et al., "Drug resistance mutations in HIV-1," International AIDS Society—USA, 10:2, pp. 11-15 (2002).

Drlica et al., "Circular DNA of human immunodeficiency virus: Analysis of circle junction nucleotide sequences," Journal of Virology, 65:1, pp. 551-555 (1991).

Finzi et al., "Identification of a reservoir for HIV-1 in patients on highly active antiretroviral therapy," Science, 278, pp. 1295-1300 (1997).

Gulizia et al., "Reduced nuclear import of human immunodeficiency virus type 1 preintegration complexes in the presence of a prototypic nuclear targeting signal," Journal of Virology, 68:3, pp. 2021-2025 (1994).

Günthard et al., "Human immunodeficiency virus replication and genotypic resistance in blood and lymph nodes after a year of potent antiretroviral therapy," J. Virol., 72:3, pp. 2422-2428 (1998).

Harrigan, "Measuring viral load in the clinical setting," Journal of Acquired Immune Deficiency Syndromes and Human Retrovirology, 10:1, pp. S34-S40 (1995).

Ho et al., "Rapid turnover of plasma virions and CD4 lymphocytes in HIV-1 infection," Nature, 373, pp. 123-126 (1995).

Hong et al., "Circular DNA of human immunodeficiency virus: Analysis of circle junction nucleotide sequences," Journal of Virology, 65:1, pp. 551-555 (1991).

Miller et al., "Human immunodeficiency virus type 1 preintegration complexes: Studies of organization and composition," Journal of Virology, 71:7, pp. 5382-5390 (1997).

Nandi, "Unintegrated viral DNA as a marker for human immunodeficiency virus 1 infection in vivo and in vitro," Acta Virologica, 43, pp. 367-372 (1999) (abstract only).

Nicholson et al., "Detection of unintegrated HIV type 1 DNA in cell culture and clinical peripheral blood mononuclear cell samples: Correlation to disease stage," AIDS Research and Human Retroviruses, 12:4, pp. 315-323 (1996).

Perelson et al., "HIV-1 dynamics in vivo: Virion clearance rate, infected cell life-span, and viral generation time," Science, New Series, 271:5255, pp. 1582-1586 (1996).

Piatek et al., "Molecular beacon sequence analysis for detecting drug resistance in mycobacterium tuberculosis, " Nature Biotechnology, 16, pp. 359-363 (1998).

Pollanova et al., "Evaluation of the effect of monotherapy with nucleoside inhibitors on plasma HIV viremia by quantitative reverse transcriptase polymerase chain reaction," Probl. Inf. Parasit. Dis., 24, pp. 2 (1997).

Popov et al., "Critical role of reverse transcriptase in the inhibitory mechanism of CNI-H0294 on HIV-1 nuclear translocation," Proc. Natl. Acad. Sci. USA, 93, pp. 11859-11864 (1996).

Shafer, "Interlaboratory variability in HIV drug resistance testing," HIVresistanceWeb (2001).

Shank et al., "Virus-specific DNA in the cytoplasm of avian sarcoma virus-infected cells is a precursor to covalently closed circular viral DNA in the nucleus," J. Virol., 25, pp. 104-114 (1978).

Sharky et al., "In vivo evidence for instability of episomal human immunodeficiency virus type 1 cDNA," Journal of Virology, 79:8, pp. 5203-5210 (2005).

Smith et al., "Analysis of long terminal repeat circle junctions of human immunodeficiency virus type 1," Journal of Virology, 64:12, pp. 6286-6292 (1990).

Stevenson et al., "Features governing nuclear import of HIV-1 preintegration complexes: Role in permissiveness, latency, and reactivation," VIII Intl. Cong. AIDS/III STD World Cong. ThA 1535 (1992) (abstract only).

Stevenson, "Molecular mechanisms for the regulation of HIV replication, persistence and latency," AIDS, 11, pp. 525-533 (1997).

Trabaud et al., "Development of a reverse transcriptase PCR-Enzyme-Linked immunosorbent assay for quantification of human immunodeficiency virus type 1 RNA in plasma: Comparison with commercial quantitative assays," Journal of Clinical Microbiology, 35:5, pp. 1251-1254 (1997).

Uberla et al., "Animal model for the therapy of acquired immunodeficiency syndrome with reverse transcriptase inhibitors," Proc. Natl. Acad. Sci., 92, pp. 8210-8214 (1995).

Wang et al., "Molecular evidence for drug-induced compartmentalization of HIV-1 quasispecies in a patient with periodic changes to HAART," AIDS, 14:15, pp. 2265-2272 (2000).

Whitcomb et al., "Sequence of the circle junction of human immunodeficiency virus type 1: Implications for reverse transcription and integration," Journal of Virology, 64:10, pp. 4903-4906 (1990).

Whitcomb et al., "The sequence of human immunodeficiency virus type 2 circle junction suggests that integration protein cleaves the ends of linear DNA asymmetrically," Journal of Virology, 65:7, pp. 3906-3910 (1991).

* cited by examiner

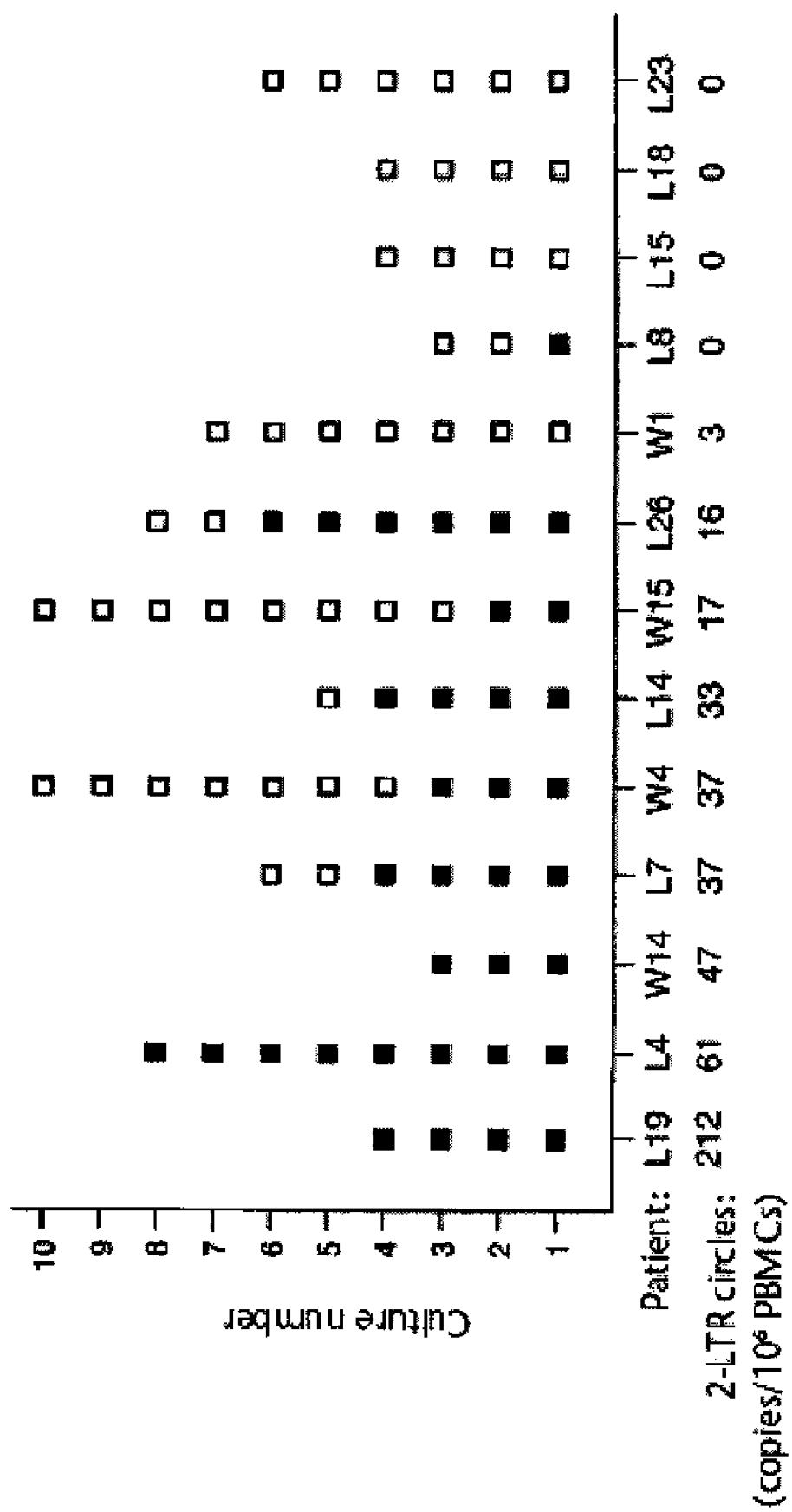

DETECTION OF HUMAN IMMUNODEFICIENCY VIRUS

CROSS-REFERENCE TO RELATED APPLICATIONS

This application is a continuation of U.S. patent application Ser. No. 10/044,197, filed Jan. 10, 2002 (now abandoned), which is a continuation of U.S. patent application Ser. No. 09/478,170, filed Jan. 5, 2000 (now abandoned), which claims the benefit of U.S. Provisional Patent Application Ser. No. 60/115,228, filed Jan. 8, 1999, all of which are incorporated herein by reference in their entirety.

STATEMENT AS TO FEDERALLY-SPONSORED RESEARCH

The invention was made with Government grants from the National Institutes of Health (RR11589, HL57880, AI32391, and AI32907). The Government has certain rights in the invention.

FIELD OF THE INVENTION

The invention relates to human immunodeficiency virus (HIV) detection assays.

BACKGROUND OF THE INVENTION

Various assays have been developed to detect HIV. A common HIV-1 detection assay utilizes quantitative polymerase chain reaction (PCR) as a means to amplify and detect viral RNA present in patient plasma. HIV-1 positive individuals undergoing combination antiviral therapy (i.e., receiving two or more anti-HIV-1 compounds) can exhibit decreased viral loads in the peripheral blood. In some cases, after several weeks or months of therapy, HIV-1 RNA cannot be detected in the peripheral blood, indicating possible eradication of HIV-1 in those individuals. Unfortunately, if patients exhibiting such a seemingly negative result stop therapy in the face of continued viral replication below the sensitivity of detection assays, the HIV can rebound very rapidly. Thus, the limited sensitivity of HIV detection assays provides a challenge to further advances in therapy.

SUMMARY OF THE INVENTION

The invention is based on the discovery that patients having no virus detectable in the blood by known means, e.g., patients undergoing drug therapy, such as combination drug therapy, can nevertheless harbor newly HIV-infected cells, and that these newly infected cells can be detected by the presence of 2-LTR circles in peripheral blood mononuclear cells. The presence of the 2-LTR circles indicates the persistence of viral spread in those patients, in spite of the fact that these patients have no detectable virus in the blood.

The invention is also based on the discovery that, for other previously HIV-positive patients without detectable virus, no 2-LTR circles are present, indicating that eradication of HIV is possible.

Accordingly, the invention features a method of detecting an HIV-infected cell (e.g., an HIV-1-infected cell) in a mammal (e.g., a human) undergoing combination anti-HIV drug therapy by detecting an HIV 2-LTR circle DNA molecule obtained from a cell (e.g., a peripheral blood mononuclear cell) of the mammal. In one embodiment of the method, cell-free HIV viral RNA cannot be detected in the blood of the mammal.

In another aspect, the invention features a method of detecting an HIV-infected cell (e.g., an HIV-1-infected cell) in a mammal (e.g., a human) by detecting an HIV 2-LTR circle DNA molecule obtained from a cell (e.g., a peripheral blood mononuclear cell) of an HIV-positive mammal (e.g., an HIV-1-positive human). In this method, cell-free HIV viral RNA cannot be detected in the blood of the mammal. In one embodiment, the mammal undergoes combination anti-HIV drug therapy.

The invention also includes a method of treatment for HIV infection in a mammal (e.g., a human) by (1) administering to the mammal (e.g., a human) one or more anti-HIV agents (e.g., one or more HIV protease inhibitors and one or more HIV reverse transcriptase inhibitors) in an amount effective to reduce an HIV viral load (e.g., circulating plasma viral load) in the mammal; and (2) detecting HIV-infected cells in the mammal using the detection methods of the invention. The treatment is continued until the level of HIV-infected cells falls below 100 (e.g., below 50, 25, 10, 5 or 1) in one million peripheral blood mononuclear cells (PBMC).

In the methods of the invention, the HIV 2-LTR circle DNA molecule can be obtained from the cell using an alkaline lysis method. In addition, the detecting step can include amplifying (e.g., by PCR) the DNA molecule before the detecting step. Examples of primers used for PCR include a (−) strand primer spanning nucleotides 9591 to 9610 of the HXB2 strain of HIV-1, and a (+) strand primer spanning nucleotides 9650-9669 of the HXB2 strain of HIV-1.

A combination anti-HIV drug therapy includes the administration of two or more antiviral compounds. Such compounds include HIV reverse transcriptase inhibitors such as zidovudine (ZDV), didanosine (ddI), and zalcitabine (ddC); and HIV protease inhibitors such as indinavir (IDV), ritonavir (RTV), saquinavir (SQV), and nelfinavir (NFV). Other compounds include inhibitors of integration, virus assembly, envelope glycoprotein binding to receptor or co-receptor, or fusion between virus and cell membranes.

An HIV-positive individual is one who produces antibodies that specifically bind to an HIV viral protein.

Cell-free HIV viral RNA is RNA that is not associated with a cell (e.g., RNA in plasma).

The methods of the invention are useful for evaluating the level of newly HIV-infected cells in HIV-positive individuals undergoing antiviral therapy. A feature of the methods is the detection of 2-LTR circles. Since 2-LTR circles exist only in the first several hours after productive infection and are degraded thereafter, they are a suitable marker for newly infected cells.

Confirmation of the eradication of HIV by the methods of the invention gives the individual or his healthcare provider the option to cease antiviral therapy. Conversely, the presence of newly infected cells during therapy, in spite of the absence of HIV RNA in the blood, signals to the healthcare provider to continue therapy. This is important because the premature cessation of therapy allows the virus to grow anew, often establishing a more persistent infection and more devastating symptoms in the patient than before antiviral therapy commenced.

Unless otherwise defined, all technical and scientific terms used herein have the same meaning as commonly understood by one of ordinary skill in the art to which this invention belongs. Although suitable methods and materials for the practice or testing of the present invention are described below, other methods and materials similar or equivalent to those described herein, which are well known in the art, can also be used. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

BRIEF DESCRIPTION OF THE DRAWINGS

FIG. 3 is a data point plot of number of virus-positive and virus-negative cultures for patient designations.

DETAILED DESCRIPTION

Figure 1A:
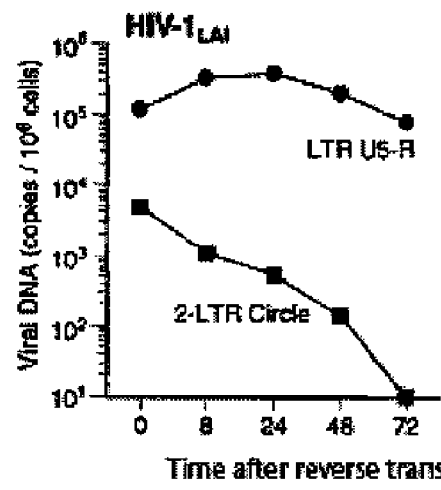
FIGS. 1A and 1B are graphs of viral DNA (copies/$10^5$ cells) versus time post RT inhibition, showing data for HIV-$1_{LAI}$ and HIV-$1_{ADA}$, respectively.

The invention relates to a method of determining the level of newly HIV-infected cells (i.e., viral spread) in HIV-positive patients, for example, patients undergoing antiviral drug therapy, by detecting HIV 2-LTR circles in the patients' cells. The method is especially useful for detecting HIV 2-LTR circles in patients testing negative for plasma viral RNA. As discussed above, patients without detectable plasma viral RNA may still retain circulating virus. Thus, complete eradication of virus from an HIV-positive individual should be confirmed by an absence of newly HIV-infected cells in that individual. The methods of the invention provide a means for that confirmation.

In vitro studies of retroviruses have shown that the first evidence of reverse transcription is unintegrated viral DNA appearing in the cytoplasm, which is transported to the nucleus within hours after infection of a cell (Shank et al., *J. Virol.*, 25:104-114, 1978; Clayman et al., *Science*, 206:582-584, 1979; and Stevenson et al., *EMBO J.*, 9:1551-1560, 1990). In the case of HIV-1, this unintegrated DNA exists in several forms, including incompletely or completely reverse-transcribed linear DNA, circular DNA containing one LTR, and circular DNA containing two LTRs (2-LTR circles). 2-LTR circles are identical to integrated proviruses, except that the ends of the LTR are joined in a head-to-tail fashion via a linker sequence of a few nucleotides.

As such, PCR can be used to specifically amplify a small segment (a few hundred base pairs) spanning the 2-LTR junction. The PCR will be specific for 2-LTR circles, since neither proviruses, single LTR circles, or other incomplete viral reverse transcription products will be amplified.

Sample Preparation

A variety of biological samples can be analyzed by the methods of the invention, including blood and solid-tissue biopsies (e.g., a lymph node biopsy). For example, blood can be collected from an HIV-positive individual undergoing combination therapy. PBMC are isolated by standard ficoll-based isolation procedures. The PBMC are then lysed and the total or extrachromosomal DNA isolated.

Total cellular DNA can be extracted by lysing the PBMC in detergent, digesting the cellular protein, and precipitating the DNA (Pauza et al., *Virology*, 205:470-478, 1984; and Panther et al., *J. Acquir. Immune. Defic. Syndr. Hum. Retro.*, 17:303-313, 1998). Extrachromosomal DNA can be isolated by any method known in the art, including standard alkaline lysis, Hirt extraction, or guanidinium thiocyanate precipitation (Jurrians et al., *J. Gen. Virol.*, 73:1537-1541, 1992; Stevenson et al., *J. Virol.* 64:2421-2425, 1990; and Sambrook et al., eds., *Molecular Cloning: A Laboratory Manual. 2nd, ed., Cold Spring Harbor Laboratory*, Cold Spring Harbor Laboratory Press, Cold Spring Harbor, N.Y., 1989).

Although the standard alkaline lysis technique is best known for isolating plasmid DNA from bacteria, this technique can also be used according to the invention to isolate 2-LTR circles from mammalian cells. The Spin Miniprep Kit available from Qiagen (Cat. No. 27104) is especially useful for this purpose. The methods of the invention include the use of this technique to isolate and purify 2-LTR circle DNA.

When possible, extrachromosomal DNA, instead of total DNA, should be isolated since the number of target 2-LTR circles per microgram of extrachromosomal DNA is expected to be far greater than the number of 2-LTR circles per microgram of total cellular DNA.

Detecting 2-LTR Circles

2-LTR circles can be detected by standard techniques which do not require nucleic acid amplification, such as Southern blotting. The DNA sample obtained as described herein can be hybridized with 2-LTR circle-specific probes that are directly or indirectly labeled with chromogenic, radioactive, fluorescent, or luminescent labels.

Where amplification of the 2-LTR circles before detection is desired, the 2-LTR circles can be detected by any amplification method well known in the art. These methods include polymerase chain reaction (PCR) (U.S. Pat. Nos. 4,683,195 and 4,683,202) and variants thereof. Another suitable nucleic acid amplification method is ligation chain reaction (LCR) or variants thereof (Landegran et al., *Science*, 241:1077-1080, 1988; and Nakazawa et al., *Proc. Natl. Acad. Sci. USA*, 91:360-364, 1994).

Other amplification methods include: self-sustained sequence replication (Guatelli et al., *Proc. Natl. Acad. Sci. USA*, 87:1874-1878, 1990), transcriptional amplification system (Kwoh, et al., *Proc. Natl. Acad. Sci. USA*, 86:1173-1177, 1989), and Q-Beta Replicase (Lizardi et al., *Bio/Technology*, 6:1197, 1988).

However the 2-LTR circles are detected, a threshold level of 2-LTR circles per million cells would be useful to define meaningful numbers of the circles. If the assay is capable of single-molecule sensitivity, a base threshold can be established at one circle per million PBMC, which is appropriate when determining whether eradication of HIV has been achieved in a patient. Whenever a patient tests above this threshold, the patient is said to exhibit active viral infection. Whenever a patient tests below the threshold, the patient is said to not exhibit active viral infection and is a candidate for removal from antiviral therapy. In other contexts, such as when the level of 2-LTR circles are used to determine the efficacy of any antiviral regiment, thresholds above one per million PBMC may be appropriate (e.g., 10, 50, 100, or 250 circles/$10^6$ PBMC).

Any of the above methods can be combined in a method of the invention to achieve suitable 2-LTR detection efficiencies.

Administration of Antiviral Drugs

The dosages, specific formulations, and routes of administration of HIV antiviral drugs are known in the art. See, eg., *Physicians' Desk Reference*, Fifty-fourth edition, Medical Economics Company, Montvale, N.J., 2000.

The invention will be further described in the following example, which does not limit the scope of the invention described in the claims.

EXAMPLE 1

Blood samples were obtained using standard techniques from 20 HIV-1-infected individuals who began and continued to receive combination anti-HIV drug therapy. All of these patients exhibited a period of time in which, after commencement of combination therapy, no plasma viral RNA could be detected by quantitative PCR. PBMC were isolated from each blood sample, and the extrachromosomal DNA was purified using the Spin Miniprep Kit available from Qiagen as Cat. No. 27104, generally following the manufacturer's directions.

HIV-1 2-LTR circles were detected by quantitative PCR using the 2-LTR-specific primers described in Stevenson et al., J. Virol., 64:2421-2425 (1990). The (−) strand primer spanned nucleotides 9591 to 9610 (or 507-526) of the HXB2 strain of HIV-1, while the (+) strand primer spanned nucleotides 9650-9669 (or 566-585) of the HXB2 strain of HIV-1 (Ratner et al., Nature, 313:277-284, 1985). Plasma viral RNA in each sample was also measured using the Amplicor HIV Monitor™ kit (Roche Molecular Systems, Inc., Branchburg, N.J.), employing HIV-1-specific quantitative PCR, following manufacturer's directions. The threshold of detection for this standard HIV-1 RNA detection assay was about 50 viral RNA molecules per milliliter of plasma. On the other hand, the threshold for the method of the invention at which the number of 2-LTR circles was conservatively estimated to give a positive result was set at 1 molecule or circle per million PBMC (roughly about 0.1 to 1 ml whole blood). Higher thresholds could be set, but such thresholds may lead to more false negatives. Considering the consequences of false negatives, the lowest practical threshold should be used. The results are summarized in Table 1.

TABLE 1

| Patient | # Viral RNA/ ml Plasma | # 2-LTR Circles/ $10^6$ cells | Months without Detectable Viral RNA |
|---|---|---|---|
| 1 | <50 | 20 | N/A |
| 2 | 155 | 25 | 8 |
| 3 | <50 | 47 | 12 |
| 4 | <50 | 872 | 9 |
| 5 | N/A | 13 | N/A |
| 6 | <50 | <1 | 9 |
| 7 | <50 | 6200 | 7 |
| 8 | <50 | <1 | 17 |
| 9 | N/A | 1 | N/A |
| 10 | <50 | 1 | N/A |
| 11 | <50 | 240 | 19 |
| 12 | 121 | 36 | 19 |
| 13 | N/A | 3 | 15 |
| 14 | <50 | 48 | 10 |
| 15 | <50 | <1 | 24 |
| 16 | <50 | 1 | 9 |
| 17 | <50 | 3 | 15 |
| 18 | <50 | <1 | 16 |
| 19 | <50 | 271 | 15 |
| 20 | 69 | 117 | 4 |

Table 1 illustrates the unexpectedly superior sensitivity of 2-LTR circle detection as compared to the standard plasma viral load assay. Some HIV-positive individuals, who do not have detectable plasma virus, nevertheless harbor newly HIV-infected blood cells, as indicated by the presence of 2-LTR circles (i.e., patients 1-5, 7, 9-14, 16, 17, 19, and 20). These individuals should not cease antiviral therapy, since infectious virus is still present in the body.

On the other hand, in some patients with undetectable plasma virus, no 2-LTR circles were detected in their PBMC (i.e., patients 6, 8, 15, and 18). These individuals may have completely eradicated HIV from their bodies, and are candidates for removal from antiviral therapy.

EXAMPLE 2

The stability of 2-LTR circle forms of viral DNA were initially examined in acutely infected cells in vitro. $CD4^+$ MT-4 T cells and Jurkat-CCR5 cells were infected with the X4 variant HIV-$1_{LAI}$ and the R5 variant HIV-$1_{ADA}$, respectively. Synthesis of viral cDNA was allowed to proceed for 24 hours, and further rounds of virus infection and cDNA synthesis were then restricted by the addition of reverse transcriptase inhibitors ZDV (5 μM) or Nevirapine (1 μM) to HIV-$1_{LAI}$ and HIV-$1_{ADA}$ infected cells, respectively. Cells were then maintained in the presence of the RT inhibitors.

The experimental procedures used in Examples 2-4 are briefly described.

The relationship between 2-LTR circle frequency and either the duration of undetectable plasma viral RNA or the frequency of positive virus co-cultures was examined using Spearman's correlation coefficient. Mean frequency of positive co-cultures in 2-LTR circle positive individuals and 2-LTR circle negative individuals as shown in FIG. 3 was further compared by a paired t-test.

Ficoll-purified PBMC (2-40×$10^6$) were collected by centrifugation at 1300×g for 2 minutes. Cell pellets were resuspended in buffer P1 and extrachromosomal DNA was purified by a QIAprep™ spin miniprep kit (Qiagen, Valencia, Calif.) using the modification for the isolation of low copy number plasmids as recommended by the manufacturer. Chromosomal DNA was recovered from the sodium acetate-SDS precipitate using DNAzol™ reagent (Life Technologies, Gaithersburg, Md.) according to the manufacturer's protocol. Total cellular DNA was purified using an Isoquick™ nucleic acid extraction kit (ORCA Research, Bothell, Wash.).

2-LTR circle junctions were amplified from 10-30 μl of extrachromosomal DNA in a 50 μl reaction containing 1× HotStarTaq™ buffer, 200 nM dNTPs, 400 nM primers, and 1.5 units HotStarTaq™ (Qiagen, Valencia, Calif.). The reverse primer was 5'-cagatctggtctaaccagaga-3' (SEQ ID NO:1), and the forward primer was 5'-gtaactagagatccctcagac-3' (SEQ ID NO:2), which annealed to nucleotides 9157-9137 (HIV-1 LTR R region) and nucleotides 130-150 (HIV-1 LTR U5 region) of HIV-$1_{LAI}$, respectively (see GenBank Accession No. K02013 for numbering). After an initial denaturation step (95° C., 10 minutes), PCR amplification proceeded for 45 cycles (95° C., 30 seconds; 60° C., 30 seconds; 72° C., 60 seconds) followed by a final extension (72° C., 5 minutes).

To control for the effect of sequence polymorphisms at primer binding sites, amplification was performed with internal primers which were reversed in orientation to those listed above. Amplification with the internal LTR primers proceeded for 35 cycles using conditions outlined above. Polymorphisms in the region of the LTR that is recognized by the fluorogenic probe can affect annealing of the probe and potentially result in "false negatives." Consequently, Taqman reaction products were subsequently analyzed on agarose-TBE gels and stained with ethidium bromide to ensure that those reactions did not contain episome-specific PCR products. For quantitation of 2-LTR circle frequency in patient PBMC, PCR reactions were performed using an ABI prism 7700 sequence detection system with the addition of 200 nM fluorogenic probe (5'-agtggcgagccctcagatgctgc-3'; SEQ ID NO:3) to the reaction. The probe anneals to nucleotides 9081-9103 of HIV-$1_{LAI}$ and was modified with 6-FAM (6-carboxyfluorescein) reporter dye on the 5' end and 6-TAMRA (6-carboxytetramethylrhodamine) quencher dye on the 3' end.

Copy number estimates of 2-LTR circles were determined by extrapolation from a plot of standards versus band intensity or by using the ABI prism 7700 quantitation software. For sequencing, 2-LTR circle junctions were cloned into a TA cloning vector (Invitrogen, San Diego, Calif.) and analyzed on an ABI 377 DNA sequencer according to the manufacturer's protocol.

Patient PBMC were separated by Ficoll-Paque (Amersham-Pharmacia) and depleted of CD8+ T lymphocytes using antibody-coated beads (Dynal). Cells were seeded in flasks in aliquots of $1\times10^7$ cells in RPMI 1640 medium supplemented with 10% fetal calf serum and activated by PHA (5 μg/ml) for 12 hours. CD8+-depleted PBMC from HIV-1 seronegative individuals were activated for 12 hours with PHA and added in equal numbers to flasks of patient PBMC together with 20 IU/ml of interleukin-2 (Genzyme). At weekly intervals, half of the culture supernatant was replaced with fresh medium containing 20 IU/ml IL-2 and $10^7$ freshly isolated, $CD^{8+}$-depleted, PHA activated donor PBMC from HIV-1 seronegative individuals. HIV-1 Gag p24 antigen in culture supernatants was evaluated by ELISA (Beckman Coulter) after 4 weeks.

Figure 1B:
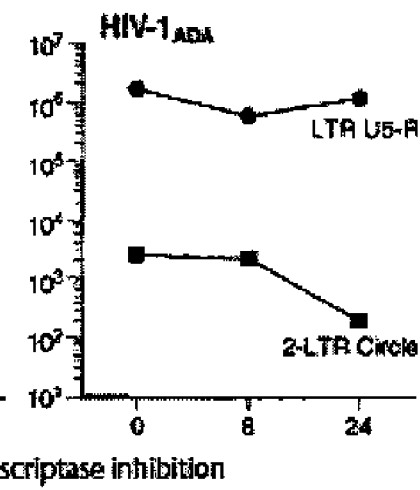

Within 24-48 hours following addition of the RT inhibitors, 2-LTR circle number fell by over ten fold in both HIV-1$_{LAI}$ and HIV-1$_{AD4}$ infected cells (FIGS. 1A and 1B). The copy number of other viral DNA forms identified by the internal LTR primers (predominantly linear and integrated viral genomes) remained relatively constant over the same interval. Thus, 2-LTR circles appeared to be labile intermediates in the virus lifecycle.

EXAMPLE 3

Figure 2A:
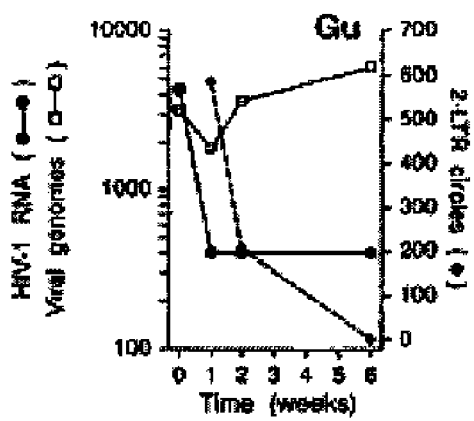
FIGS. 2A-2D are graphs of HIV-1 RNA or genomes versus time in weeks, showing the data for patients Gu, Sm, Za, and Ha, respectively.
Figure 2B:
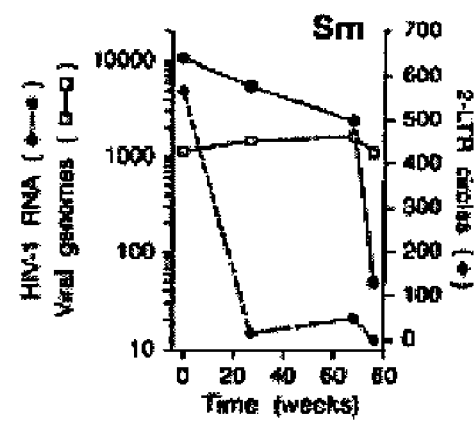
Figure 2C:
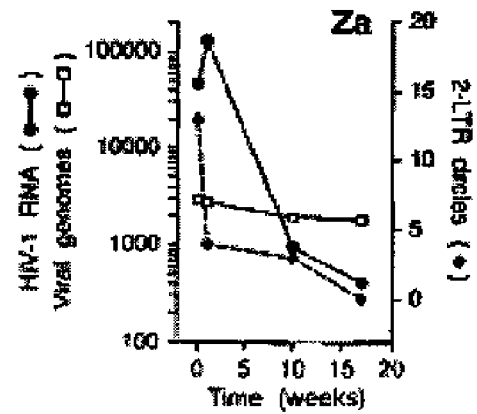
Figure 2D:
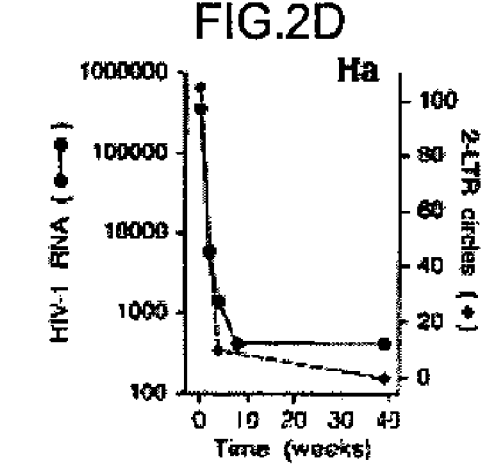

Whether 2-LTR circles were labile in vivo was next evaluated. PBMC samples were obtained from four HIV-1 infected individuals (Gu, Sm, Za, Ha) who, following adjustment of their antiretroviral regimens to more potent combinations, exhibited steady declines in plasma viral RNA levels. Patient Gu, who had been maintained on a two-drug RT inhibitor combination, was subsequently changed (week 0) to a three-drug regimen (ZDV/3TC/NFV). Patient Sm, who had been on a two-drug regimen (ZDV/3TC) was changed at week 68 to ddI/EFV/NFV. Patient Za, who had been on a four-drug regimen (3TC/D4T/ddI/NFV) was adjusted (week 1) to ZDV/ddC/NFV/RTV. Patient Ha, previously on a three-drug regimen (ZDV/ddI/NVP) was subsequently adjusted (week 0) to D4T/3TC/NVP. Marked declines in 2-LTR circle copy number were observed over the interval in which there was a rapid drop in levels of plasma viral RNA (FIGS. 2A-2D). In contrast, when samples were analyzed in parallel with internal LTR primers, HIV-1 viral genome levels (detected via cDNA) fluctuated by no more than three fold (FIGS. 2A-2C). Collectively, the results suggest that 2-LTR circles are labile, both in vitro and in vivo, relative to integrated viral genomes.

EXAMPLE 4

A larger patient population than that of Example 1 was then examined. The 2-LTR HIV-1 episomes were examined in 63 patients (four of whom were included in the study described in Example I) who, through treatment with high activity antiretroviral therapy (HAART), had undetectable levels of plasma viral RNA for sustained periods of time (Table 2). Fifty of these patients (80%) had undetectable levels of plasma viral RNA (assay limit of sensitivity was 400 copies/ml) for 12 months or longer (Table 2). Of these 50 patients, 24 (48%) exhibited undetectable levels of plasma viral RNA for 12 months or more using an assay with a sensitivity of 50 copies/ml. In 48 of the 63 patients (76%), 2-LTR circles were detected in their PBMC (Table 2). 2-LTR circle copy numbers ranged from less than 1 copy/$10^6$ PBMC to 620 copies/$10^6$ PBMC. There did not appear to be any significant relationship between the frequency of 2-LTR circles in patient PBMC and the time during which plasma viral RNA was undetectable. This data indicated that labile replication intermediates are present in a substantial proportion of HIV-1 infected individuals who exhibit sustained suppression of plasma viral RNA while on HAART. 2-LTR circles were not detectable in PBMC from 15 (24%) patients (Table 2).

Table 2 below lists AIDS patients on HAART and the level of 2-LTR circles and viral RNA in the blood. The abbreviations for Table 2 are as follows. Anti-retroviral therapy: ZDV, Zidovudine; 3TC, Lamivudine; D4T, Stavudine; ddI, Didanosine; NVP, Nevirapine; RTV, Ritonavir; EFV, Efavirenz; SQV, Saquinavir; IDV, Indinavir; NFV, Nelfinavir; ddC, Zalcitabine; and ABV, Abacavir. CD4+ T cell measurements were determined at or just prior to time PBMC were collected for PCR analysis of viral cDNA intermediates.

For the column labeled "Period of Undetectable Viral RNA," plasma viral RNA was detected using an assay with a sensitivity of about 400 copies/ml. Numbers in parentheses indicated the period for which viral RNA was below the level of detection using a second assay with a sensitivity of 50 copies/ml. Plasma viral RNA measurements were determined approximately every three months.

The 2-LTR circle copy number in most cases were determined in duplicate on independent PBMC samples. Values less than 1 indicated that more than 1 million PBMC were required for detection of 2-LTR circles.

The total number of PBMC from which extrachromosomal DNA was isolated and analyzed for the presence of 2-LTR circles was determined as follows. In all patients, 2-LTR circles were quantitated by fluorescence-based PCR using Taqman software (ABI Prism 7700 Software). Similar 2-LTR circle numbers were obtained when samples were quantitated by comparison of PCR band intensity to a standard dilution of synthetic 2-LTR circles.

TABLE 2

| Patient Number | Drug Regiments | CD4+ T Cells (cells/ml) | Period of Undetectable Viral RNA (months) | 2-LTR circles (Copies/$10^6$ PBMC) | #PBMC Analyzed (millions) |
|---|---|---|---|---|---|
| W1 | RTV, ZDV, 3TC | 475 | 23 (14) | 3 | 1.0 |
| W2 | NFV, ZDV, 3TC | 827 | 13 (13) | <1 | 5.5 |
| W3 | IDV, D4T, 3TC | 436 | 23 (14) | 27 | 1.0 |
| W4 | IDV, D4T, 3TC | 505 | 22 (12) | 37 | 1.0 |
| W6 | IDV, D4T, 3TC | 248 | 19 (11) | 15 | 1.0 |
| W7 | SQV, D4T, 3TC | 443 | 19 (13) | 8 | 1.0 |
| W8 | ddl, D4T | 870 | 18 (15) | <1 | 4.0 |
| W9 | NFV, D4T, 3TC | 641 | 22 (11) | 59 | 1.0 |
| W10 | IDV, ZDV, 3TC | 656 | 22 (15) | <1 | 4.0 |
| W11 | IDV, ZDV, 3TC | 344 | 22 (15) | 65 | 1.0 |
| W12 | ZDV, 3TC, DLV | 626 | 26 (16) | <1 | 5.5 |
| W13 | NFV, ZDV, 3TC | 699 | 13 (13) | <1 | 5.5 |
| W14 | NFV, D4T, 3TC | 685 | 21 (15) | 47 | 1.0 |
| W15 | NFV, STC, NVP | 866 | 25 (12) | 17 | 1.0 |
| W16 | RTV, D4T, 3TC | 572 | 22 (14) | 2 | 5.5 |
| W17 | IDV, ZDV, 3TC | 364 | 26 (15) | 31 | 1.0 |
| W18 | IDV, ZDV, 3TC | 119 | 21 (16) | <1 | 2.0 |
| W19 | SQV, ZDV, 3TC | 153 | 16 (10) | 4 | 4.0 |
| W20 | IDV, ZDV, 3TC | 360 | 27 (15) | <1 | 4.0 |
| W21 | NFV, D4T, 3TC | 208 | 13 (13) | <1 | 2.0 |
| W22 | D4T, 3TC | 495 | 23 (15) | <1 | 4.0 |
| W28 | NFV, ddl, D4T | 527 | 22 (8) | 9 | 1.0 |
| W30 | D4T, 3TC | 575 | 22 (17) | <1 | 4.0 |

TABLE 2-continued

| Patient Number | Drug Regiments | CD4+ T Cells (cells/ml) | Period of Undetectable Viral RNA (months) | 2-LTR circles (Copies/ $10^6$ PBMC) | #PBMC Analyzed (millions) |
|---|---|---|---|---|---|
| M1 | NFV, D4T, NVP | 287 | 14 (9) | 31 | 1.0 |
| M3 | IDV, ddl, NVP | 440 | 16 (7) | 22 | 1.0 |
| M4 | IDV, ZDV, 3TC | 586 | 13 (ND) | 264 | 1.0 |
| M6 | NFV, ZDV, 3TC | 317 | 24 (7) | 63 | 1.0 |
| M7 | NFV, 3TC, NVP | 175 | 11 (ND) | 4 | 5.5 |
| M8 | IDV, ZDV, 3TC, NVP | 357 | 13 (2) | 15 | 1.0 |
| M12 | NFV, D4T, 3TC | 749 | 12 (7) | 35 | 1.0 |
| M13 | ZDV, 3TC, EFV | 670 | 10 (0) | 67 | 1.0 |
| M14 | IDV, ZDV, 3TC | 728 | 14 (14) | 41 | 1.0 |
| M15 | IDV, ZDV, 3TC | 565 | 10 (10) | 82 | 1.0 |
| M16 | NFV, 3TC, NVP | 403 | 12 (8) | 3 | 4.0 |
| L2 | 3TC, D4T, RTV | 852 | 8 (8) | 5 | 1.0 |
| L3 | ZDV, 3TC, IDV | 448 | 12 (8) | 10 | 1.0 |
| L4 | ZDV, 3TC, RTV | 978 | 21 (12) | 180 | 1.0 |
| L6 | D4T, RTV, SQV | 577 | 10 (7) | <1 | 4.0 |
| L7 | D4T, ddl, NVP | 394 | 11 (7) | 610 | 1.0 |
| L8 | ZDV, 3TC, NFV | 173 | 17 (8) | <1 | 1.0 |
| L9 | 3TC, D4T, EFV | 482 | 8 (5) | <1 | 2.2 |
| L11 | ZDV, 3TC, RTV | 615 | 19 (12) | 84 | 1.0 |
| L12 | 3TC, D4T, RTV | 389 | 19 (6) | 7 | 1.0 |
| L13 | D4T, SQV, NFV | 312 | 15 (3) | <1 | 7.8 |
| L14 | 3TC, D4T, IDV | 375 | 14 (7) | 116 | 1.0 |
| L15 | 3TC, RTV, SQV, ABV | 91 | 30 (17) | <1 | 1.5 |
| L16 | 3TC, D4T, SQV, RTV | 575 | 12 (12) | 4 | 8.1 |
| L17 | 3TC, D4T, SQV | 198 | 15 (15) | 14 | 1.0 |
| L18 | ZDV, 3TC, IDV | 175 | 16 (13) | <1 | 10.2 |
| L19 | 3TC, D4T, RTV, SQV | 499 | 15 (6) | 620 | 1.0 |
| L22 | ZDV, D4T, IDV | 223 | 14 (12) | 6 | 1.0 |
| L23 | 3TC, ddC, IDV | 534 | 14 (12) | <1 | 4.8 |
| L26 | 3TC, D4T, SQV, NFV | 911 | 17 (6) | 36 | 1.0 |
| L27 | ZDV, 3TC, IDV | 185 | 17 (17) | <1 | 3.2 |
| L28 | D4T, ABV, EFV | 80 | 8 (8) | 275 | 1.0 |
| L29 | ZDV, ddC, SQV, NFV | 121 | 21 (1) | 3 | 2.0 |
| L32 | 3TC, D4T, EFV | 219 | 7 (1) | <1 | 10.0 |
| L33 | 3TC, D4T, IDV | 610 | 16 (1) | <1 | 14.4 |
| L36 | ddl, D4T, NFV | 172 | 14 (4) | 2 | 5.6 |
| L37 | ZDV, ddC, 3TC, IDV | 279 | 13 (7) | <1 | 5.6 |
| L41 | ZDV, 3TC, RTV | 990 | 22 (1) | 100 | 1.0 |
| L42 | 3TC, D4T, SQV | 117 | 18 (1) | <1 | 2.0 |
| L46 | 3TC, D4T, NFV | 180 | 7 (1) | 4 | 20.0 |

It was suspected that in 2-LTR circle positive patients, there would also be cells harboring replication competent virus. To investigate this, high-input viral co-culture assays were performed on PBMC from nine 2-LTR circle positive and four 2-LTR circle negative patients. The results are shown in FIG. 3. Replication competent virus could readily be isolated from eight of the nine patients who were 2-LTR circle positive. Virus could not be isolated from patient W1 who had a very low circle copy number. Intriguingly, infectious virus could not be isolated from three patients who were 2-LTR circle negative even though co-culture was conducted on between 40 and 60 million CD8+-depleted patient PBMC. In patient L8 who was also 2-LTR circle negative, only one of three cultures yielded infectious virus (FIG. 3). Collectively, these results suggested a correlation between the presence of 2-LTR circles and cells harboring replication competent virus. Plasma based viral RNA assays therefore, unlike the 2-LTR circle assay, failed to reveal the full extent of viral activity in infected individuals who are being treated with HAART.

This study has important implications for the development of strategies to eradicate virus replication in HIV-1 infected individuals. Although complete elimination of HIV-1 replication may be difficult with current antiretroviral regimens, this study suggests instances in which even the most sensitive assays fail to reveal ongoing replication in some well suppressed patients. It is also likely that, as more potent antiretrovirals enter the clinic, ongoing or "covert" virus replication may be arrested in a higher percentage of patients. A better understanding of the nature of the reservoir which sustains virus replication in aviremic patients on HAART may lead to the development of more effective strategies for arrest of virus replication. Monitoring of the 2-LTR, as a superior surrogate marker for viral replication, can be integral to the understanding of viral reservoirs.

Other Embodiments

It is to be understood that while the invention has been described in conjunction with the detailed description thereof, the foregoing description is intended to illustrate and not limit the scope of the invention, which is defined by the scope of the claims. Other aspects, advantages, and modifications are within the scope of the following claims.

What is claimed is:

1. A method of detecting ongoing Human Immunodeficiency Virus (HIV) replication in a mammal undergoing combination anti-HIV drug therapy, the method comprising:
   determining that less than about 50 cell-free HIV viral RNA molecules per milliliter of plasma can be detected in the mammal, and
   detecting an HIV 2-long terminal repeat (2-LTR) circle DNA molecule in a sample comprising a cell obtained from the mammal,
wherein the presence of a 2 LTR circle DNA indicates the presence of ongoing HIV replication in the mammal.

2. The method of claim 1, further comprising amplifying the DNA molecule before the detecting step.

3. The method of claim 2, wherein the DNA molecule is amplified using polymerase chain reaction.

4. The method of claim 1, wherein the drug therapy comprises administering to the mammal at least one HIV reverse transcriptase inhibitor.

5. The method of claim 4, wherein the drug therapy further comprises administering to the mammal at least one HIV protease inhibitor.

6. The method of claim 1, wherein the drug therapy comprises administering to the mammal at least one HIV protease inhibitor.

7. The method of claim 1, wherein the mammal is a human.

8. The method of claim 1, wherein the mammal is a human.

9. The method of claim 1, wherein the cell is a peripheral blood mononuclear cell.

10. The method of claim 1, wherein cell-free HIV viral RNA cannot be detected in the blood of the mammal.

11. A method of detecting ongoing Human Immunodeficiency Virus (HIV) replication in an HIV-1-positive mammal, the method comprising:
   determining that less than about 50 cell-free HIV viral RNA molecules per milliliter of plasma can be detected in the mammal, and
   detecting an HIV 2-long terminal repeat (2-LTR) circle DNA molecule in a sample comprising a cell obtained from the mammal,
wherein the presence of a 2 LTR circle DNA indicates the presence of ongoing replication in the mammal.

12. The method of claim 11, further comprising amplifying the DNA molecule before the detecting step.

13. The method of claim 12, wherein the DNA molecule is amplified using polymerase chain reaction.

14. The method of claim 11, wherein the mammal is a human.

15. The method of claim 11, wherein the cell is a peripheral blood mononuclear cell.

16. A method of detecting a Human Immunodeficiency Virus (HIV)-infected peripheral blood mononuclear cell (PBMC) in an individual, the method comprising:
   determining that less than about 50 cell-free HIV viral RNA molecules per milliliter of plasma can be detected in the individual;
   amplifying an HIV-1 2-long terminal repeat (2-LTR) circle DNA molecule obtained from a PBMC of an HIV 1-positive individual undergoing combination anti-HIV-1 drug therapy to produce an amplified nucleic acid; and
   detecting the amplified nucleic acid, wherein the presence of the amplified nucleic acid indicates the presence of an HIV-infected PBMC.

17. A method of claim 1, further comprising obtaining the HIV 2-LTR circle DNA molecule using an alkaline lysis method.

18. A method of claim 3, wherein the primers used for PCR comprise a (−) strand primer spanning nucleotides 9591 to 9610 of the HXB2 strain of HIV-1, and a (+) strand primer spanning nucleotides 9650 9669 of the HXB2 strain of HIV-1.

19. A method of treatment for HIV infection in a mammal, the method comprising:
   determining that less than about 50 cell-free HIV viral RNA molecules per milliliter of plasma can be detected in the mammal;
   administering to the mammal one or more anti-HIV agents in an amount effective to reduce an HIV viral load in the mammal; and
   detecting HIV-infected cells in the mammal using the method of claim 16,
   wherein treatment is continued at least until the level of HIV-infected PBMCs falls below one in one million peripheral blood mononuclear cells.

20. The method of claim 1, wherein the cell is from a solid tissue biopsy.

21. The method of claim 11, wherein the cell is from a solid tissue biopsy.

22. A method of treatment for HIV infection in a mammal, the method comprising:
   administering to the mammal one or more anti-HIV agents in an amount effective to reduce an HIV viral load in the mammal;

determining that less than about 50 cell-free HIV viral RNA molecules per milliliter of plasma can be detected in the mammal; and detecting ongoing HIV replication in the mammal by detecting an HIV 2-long terminal repeat (2-LTR) circle DNA molecule in a sample comprising a cell obtained from the mammal, wherein the presence of 2-LTR circle DNA indicates the presence of ongoing HIV replication, wherein treatment is continued at least until HIV replication is no longer detectable.

23. The method of claim 22, wherein the cell is a peripheral blood mononuclear cell.

24. The method of claim 22, wherein the mammal is a human.

* * * * *

UNITED STATES PATENT AND TRADEMARK OFFICE
CERTIFICATE OF CORRECTION

PATENT NO.         : 7,507,527 B2
APPLICATION NO. : 10/795580
DATED              : March 24, 2009
INVENTOR(S)        : Mario Stevenson It is certified that error appears in the above-identified patent and that said Letters Patent is hereby corrected as shown below:

On page 1, col. 2 (Other Publications), line 1, delete "resevoir" and insert --reservoir--
On page 1, col. 2 (Other Publications), line 15, delete "unitegrated" and insert --unintegrated--
On page 1, col. 2 (Other Publications), line 36, delete "respone" and insert --response--
In claim 1, col. 11, line 31, delete "2 LTR" and insert --2-LTR--
In claim 11, col. 11, line 62, delete "2 LTR" and insert --2-LTR--
In claim 18, col. 12, line 45 (approx.), delete "9650 9669" and insert --9650-9669--

Signed and Sealed this

Ninth Day of June, 2009

JOHN DOLL
*Acting Director of the United States Patent and Trademark Office*

UNITED STATES PATENT AND TRADEMARK OFFICE
CERTIFICATE OF CORRECTION

PATENT NO.         : 7,507,527 B2                                                Page 1 of 1
APPLICATION NO.    : 10/795580
DATED              : March 24, 2009
INVENTOR(S)        : Stevenson It is certified that error appears in the above-identified patent and that said Letters Patent is hereby corrected as shown below:

On the cover page,

Item [*] Notice: Subject to any disclaimer, the term of this patent is extended or adjusted under 35 USC 154(b) by 313 days.

Delete the phrase "by 313 days" and insert --by 311 days--

Signed and Sealed this

Twenty-seventh Day of October, 2009

David J. Kappos
*Director of the United States Patent and Trademark Office*

SEQUENCE LISTING

<160> NUMBER OF SEQ ID NOS: 3

<210> SEQ ID NO 1
<211> LENGTH: 21
<212> TYPE: DNA
<213> ORGANISM: Artificial Sequence
<220> FEATURE:
<223> OTHER INFORMATION: Primer

<400> SEQUENCE: 1
cagatctggt ctaaccagag a                    21

<210> SEQ ID NO 2
<211> LENGTH: 21
<212> TYPE: DNA
<213> ORGANISM: Artificial Sequence

```
-continued

<220> FEATURE:
<223> OTHER INFORMATION: Primer

<400> SEQUENCE: 2
gtaactagag atccctcaga c                                              21

<210> SEQ ID NO 3
<211> LENGTH: 23
<212> TYPE: DNA
<213> ORGANISM: Artificial Sequence
<220> FEATURE:
<223> OTHER INFORMATION: Probe sequence

<400> SEQUENCE: 3
agtggcgagc cctcagatgc tgc                                            23
```